(12) United States Patent
Osta

(10) Patent No.: US 9,078,986 B2
(45) Date of Patent: Jul. 14, 2015

(54) ADJUSTABLE LARYNGEAL AIRWAY (ALA) DEVICE AND METHOD OF USE

(75) Inventor: Walid Osta, Dearborn Heights, MI (US)

(73) Assignee: ALA DEVICE, LLC, Canton, MI (US)

( * ) Notice: Subject to any disclaimer, the term of this patent is extended or adjusted under 35 U.S.C. 154(b) by 866 days.

(21) Appl. No.: 13/294,292

(22) Filed: Nov. 11, 2011

(65) Prior Publication Data

US 2013/0118501 A1    May 16, 2013

(51) Int. Cl.
*A61M 16/04*    (2006.01)
*A61M 16/06*    (2006.01)

(52) U.S. Cl.
CPC ........... *A61M 16/04* (2013.01); *A61M 16/0488* (2013.01)

(58) Field of Classification Search
CPC ............ A61M 16/04; A61M 16/0429; A61M 16/0488; A61M 16/0493; A61M 16/0495; A61M 16/0497; A61F 2002/30411; A61F 2002/30538; A61F 2250/0006
USPC .......................... 128/200.26, 204.18, 206.29, 128/207.14–207.18, 207.29; 606/196, 198, 606/108; 600/185, 190, 193–197; 604/19, 604/23–28, 43, 45, 48, 93.01, 131, 140, 604/147, 500, 514, 275, 278–279; 623/1.11
See application file for complete search history.

(56) References Cited

U.S. PATENT DOCUMENTS

| | | | | |
|---|---|---|---|---|
| 1,434,964 A | * | 11/1922 | Rose | 604/108 |
| 1,632,541 A | * | 6/1927 | Cortes | 604/107 |
| 3,642,005 A | | 2/1972 | McGinnis | |
| 3,968,800 A | * | 7/1976 | Vilasi | 606/198 |
| 5,263,478 A | * | 11/1993 | Davis | 128/207.14 |
| 5,303,697 A | | 4/1994 | Brain | |
| 5,498,231 A | * | 3/1996 | Franicevic | 600/190 |
| 5,996,582 A | | 12/1999 | Turnbull | |
| 7,001,094 B2 | | 2/2006 | Ami et al. | |
| 7,556,042 B2 | | 7/2009 | West et al. | |
| 8,104,468 B2 | * | 1/2012 | Chen et al. | 128/200.26 |
| 2004/0200479 A1 | | 10/2004 | Chang | |
| 2005/0066975 A1 | | 3/2005 | Brain | |
| 2006/0076023 A1 | | 4/2006 | Rapacki et al. | |
| 2007/0295336 A1 | | 12/2007 | Nelson et al. | |
| 2007/0295337 A1 | | 12/2007 | Nelson et al. | |
| 2008/0078401 A1 | | 4/2008 | O'Neil et al. | |
| 2008/0078404 A1 | | 4/2008 | Martens | |
| 2008/0078405 A1 | | 4/2008 | Crumback et al. | |
| 2008/0236593 A1 | | 10/2008 | Nelson et al. | |
| 2009/0194113 A1 | * | 8/2009 | Chen et al. | 128/207.14 |
| 2010/0313894 A1 | | 12/2010 | Crumback et al. | |
| 2010/0313895 A1 | | 12/2010 | O'Neil et al. | |
| 2010/0313896 A1 | | 12/2010 | O'Neil et al. | |

FOREIGN PATENT DOCUMENTS

WO        95/33506 A1    12/1995

* cited by examiner

*Primary Examiner* — Tan-Uyen (Jackie) T Ho
*Assistant Examiner* — Mark K Han
(74) *Attorney, Agent, or Firm* — Gifford, Krass, Sprinkle, Anderson & Citkowski, P.C.

(57) ABSTRACT

An adjustable laryngeal airway or airflow control apparatus and method to control air flow into and out of the body including a tube having an inner surface and an outer surface including a threaded portion. The adjustable laryngeal airway (ALA) includes at least one arm having a first portion and a second portion wherein the first portion is laterally spaced apart from the second portion. The arms include structure such as grooves, threads, or slots operable to connect with the threading on the outer surface of the tube. A mask is fitted around the outer surface of the tube to create a seal in the system. The tube engages the thread on the outer surface of the tube to allow the at least one arm to pivot about the first portion allowing the arms to rotate away from the tube.

17 Claims, 4 Drawing Sheets

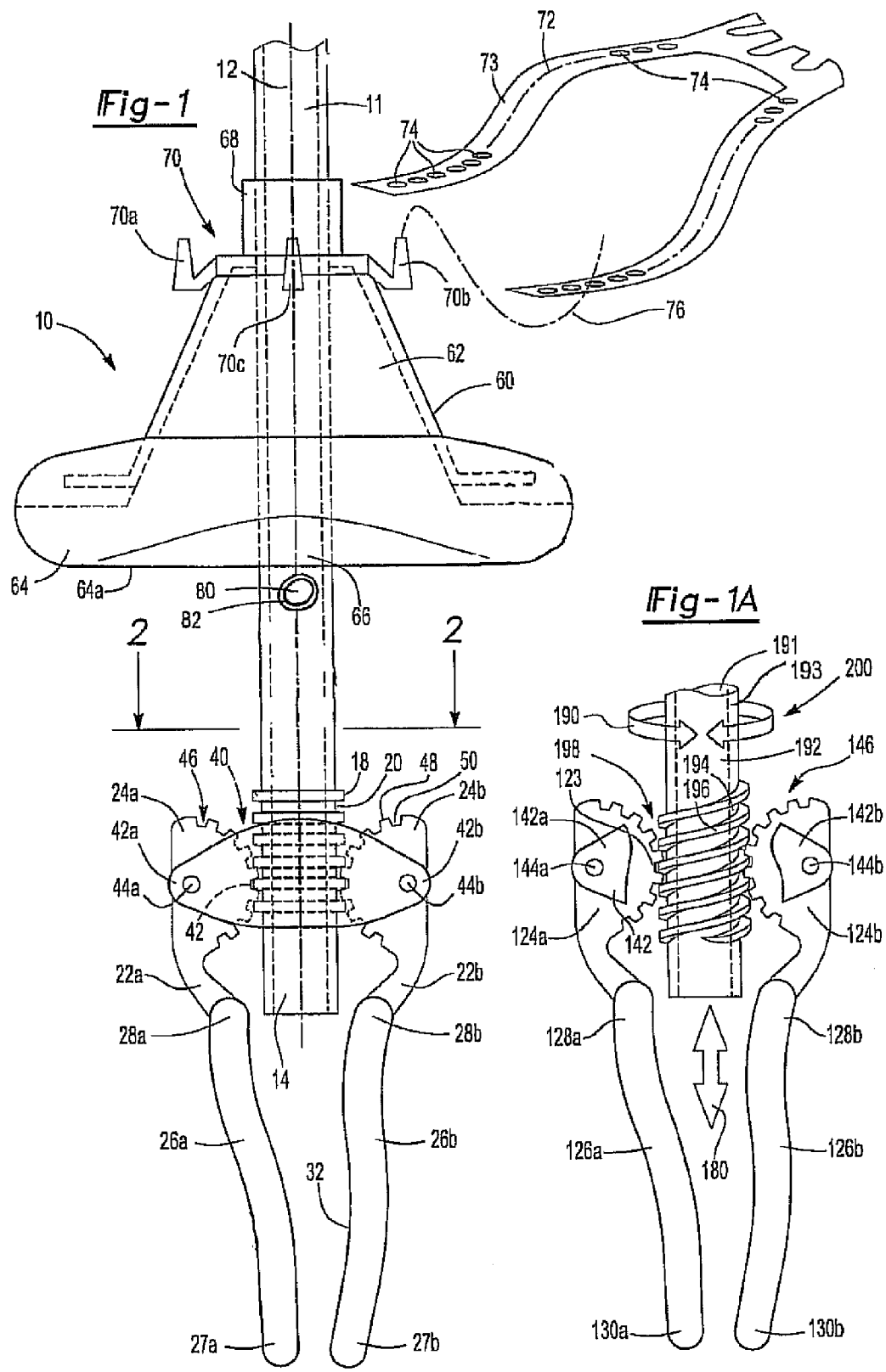

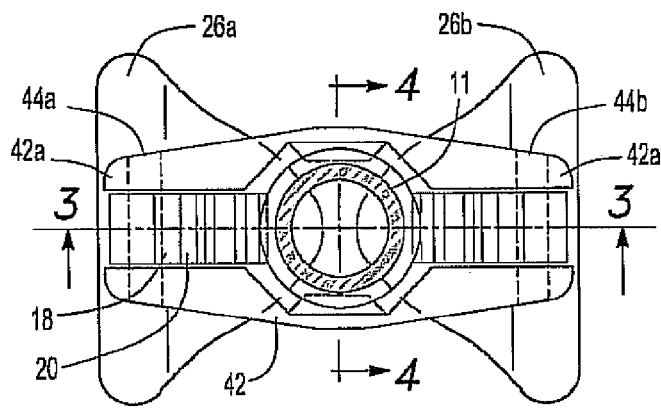
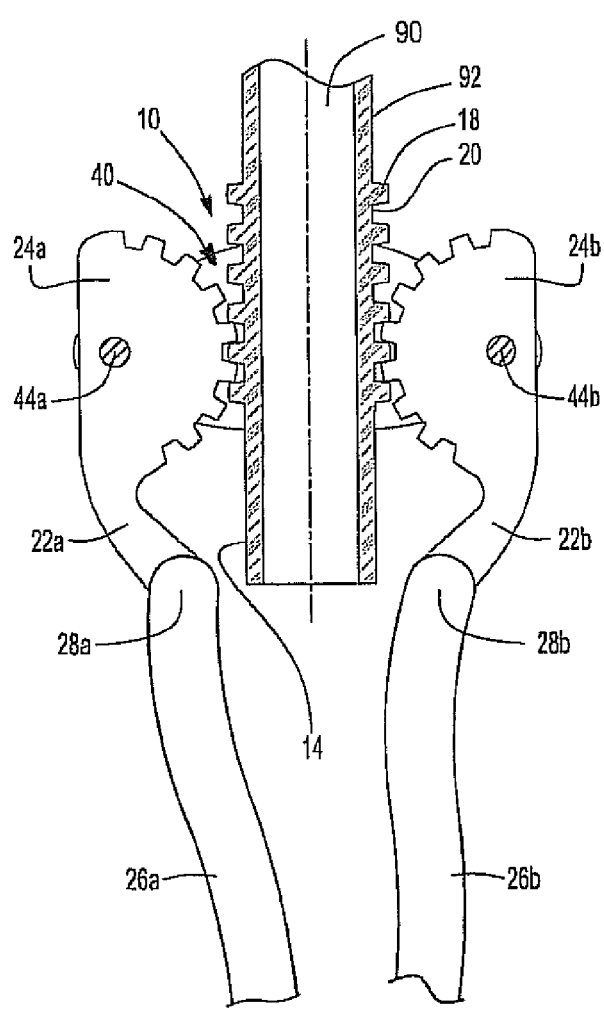
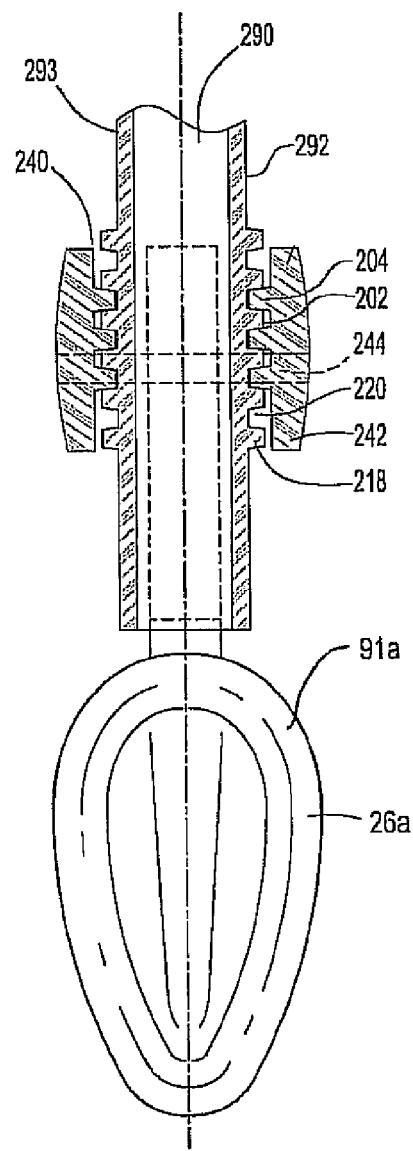

ADJUSTABLE LARYNGEAL AIRWAY (ALA) DEVICE AND METHOD OF USE

FIELD OF THE INVENTION

This invention relates generally to airflow control devices. More particularly, this invention relates to a laryngeal airway device and method for use to control air flow in the body of a human being.

BACKGROUND OF THE INVENTION

Endotracheal intubation tube is a typical and effective device for providing air flow to the lungs of a patient, particularly an unconscious patient under general anesthesia. For air or oxygen to reach the human lungs, it has to travel through a patent conduit through the mouth, the vocal cords, the larynx, the trachea, and down to the lungs. The endotracheal intubation tube (hereinafter known as EIT) comprises a flexible tube which commonly has an inflatable cuff near its distal end. The EIT is inserted into the trachea, which is the tube like structure that connects the mouth and the larynx to the lungs, in a procedure called "intubation." Intubation is usually performed by a trained medical professional, commonly an anesthesiologist, when the patient is unconscious due to general anesthesia or a certain medical emergency that causes loss of consciousness such as trauma, seizures, heart attacks or other. Intubation is done by inserting an "intubation blade" held by one hand into the mouth of the patient and inserting the EIT, held by the other hand, into the trachea under direct vision of the vocal cords, which constitute the door to the larynx. Intubation is usually done to ensure that the unconscious patient, while unable to breathe spontaneously, will still receive oxygen to his or her lungs, which is an indispensible process in order to maintain life. However, in many patients, conventional intubation as described above is very difficult or impossible and often is ineffective due to provider related factors (lack of expertise or specialized training), or more commonly patient's related factor (obesity, unusual anatomy, swelling of the soft tissues due to fluids or trauma or many other factors) which hinder the direct visualization of the tracheal opening or access of the EIT to the trachea. This usually results in bad consequences to the patients including death, permanent brain damage and/or heart attacks within few minutes after loss of oxygen flow to the lungs.

U.S. Patent Application Publication No. 2010/0313895 discloses an adjustable endotracheal tube adapted to increase in diameter after the tube is placed into the trachea. The adjustable endotracheal tube improves upon previously known endotracheal tubes in that it allows for adjustment of the diameter of the tube by means of a balloon. The balloon is used to seal against the tracheal passageway. The balloon conforms to the trachea walls to form the air seal. This device does not provide any advantage over the traditional EIT as a rescue device since it must be placed in the trachea in an identical way to the traditional EIT, and it actually could be more difficult to place due to its bigger size compared to the traditional EIT.

A laryngeal mask airway is used on the patient when the traditional endotracheal intubation is not effective. The laryngeal mask airway (hereinafter LMA) comprises an airway tube and an inflatable mask at the distal end of the airway tube. The mask can easily be inserted into the pharynx of the patient and then inflated to seal against the laryngeal inlet. LMAs come in a variety of sizes ranging from large adult sizes to infant sizes. The laryngeal mask functions as a peripharyngeal sealer. The LMA includes an open end pointing down towards the tongue which pushes back towards the uvula. The cuff follows the natural bend of the oropharynx, and is seated over the pyriform fossae. Once in position, the cuff around the mask is slightly inflated to create a tight air seal. The LMA is not inserted into the trachea as with the EIT but lies in the posterior compartment of the mouth, in proximity to the laryngeal inlet, which is the entry point of the human respiratory system.

U.S. Pat. No. 5,623,921 granted to Kinsinger et al. discloses a laryngeal mask airway similar to the LMA as described above. The airway tube includes a first tube section having a distal end connected to the mask and a second separable tube allowing it to split away from the first tube. The LMAs as disclosed in the '921 patent are well known and common representations of LMAs known in the field of anesthesia.

However, the EITs and LMAs as disclosed above are often still not effective to resuscitate the unconscious patient. LMA is NOT a perfect device. The main advantages of the LMA are that it is much easier to use, it could be placed in position in a relatively shorter time than an EIT in an emergency situation, and, it does not require a highly trained personnel to place it. The biggest disadvantage is that LMA does NOT provide a direct connection to the trachea with resulting high probability of failure to guarantee the flow of oxygen to the lungs. Death and other severe injuries still occur despite the appropriate use of the LMA. The main reason is that soft tissues in the mouth become relaxed, heavy and redundant after the patient loses consciousness, thus collapsing into the mouth and potentially preventing any air flow from the mouth, where the LMA is situated, to the trachea. If the EIT is ineffective, the medical personnel will frequently reach for the LMA to resuscitate the patient. If the LMA is ineffective to resuscitate the patient, the personnel is left with very limited options to save the patient's life, which are most likely surgical and require the immediate availability of a surgeon who is trained to make a surgical opening in the neck in order to bypass the mouth.

Accordingly, there exists a need in the art to provide an adjustable airway device with similar advantage to the LMA but which will operate to displace the soft tissues in the mouth of the unconscious patient so as to facilitate air flow into and/or out of the lungs of a patient thereby resuscitating the patient and saving the patient's life.

SUMMARY OF THE INVENTION

The present invention provides for an adjustable laryngeal airway or airflow control apparatus to control air flow into and out of the body. The apparatus includes a tube having an inner surface and an outer surface wherein the inner surface includes a surface freely permitting air flow and the outer surface including a threaded portion. Further, the adjustable laryngeal airway (hereinafter known as ALA) device includes at least one arm, typically two arms, having a first portion and a second portion wherein the first portion is laterally spaced apart from the second portion. The arms include structure such as grooves, threads, or slots operable to connect with the threading on the outer surface of the tube. A ring further connects the at least one arm to a second arm and secures the arms to the tube. Further, a mask is fitted around the outer surface of the tube to create a seal in the system. During use, the ALA is inserted in the mouth of the unconscious patient and will lie in the posterior compartment of the mouth, in proximity to the laryngeal inlet, which is the entry point of the human respiratory system. Subsequently, the user of the apparatus is able to twist or push the tube with one hand while holding the ALA at the level of the ring with the other hand, thereby engaging the thread on the outer surface of the tube to allow the at least one arm to pivot about the first portion allowing the arms to rotate away from the tube. Holding the ALA in place with one hand, while the other hand is twisting the tube, will allow the arms to migrate away from the tube in a vertical direction (assuming the patient is resting in a horizontal position) while avoiding the twisting of the device in the mouth. As the arms rotate away from the tube, any soft tissue preventing air flow is elevated or pushed aside to permit air flow. The threading on the tube may either be helical or designed as a worm gear thereby dictating whether the user should twist or push the tube to engage the arms.

BRIEF DESCRIPTION OF THE DRAWINGS

FIG. 1 illustrates a side view and perspective view of the complete adjustable laryngeal airway assembly;

FIG. 1A illustrates a second embodiment of the distal end of the adjustable laryngeal mask as shown in FIG. 1;

FIG. 2 illustrates a top view of the adjustable laryngeal mask as shown in FIG. 1;

FIG. 3 illustrates a cross sectional side view of the adjustable laryngeal mask as shown in FIG. 2;

FIG. 4 illustrates a cross sectional side view of an alternative embodiment of the adjustable laryngeal mask as shown in FIG. 2;

DETAILED DESCRIPTION OF THE DRAWINGS

Figure 5:
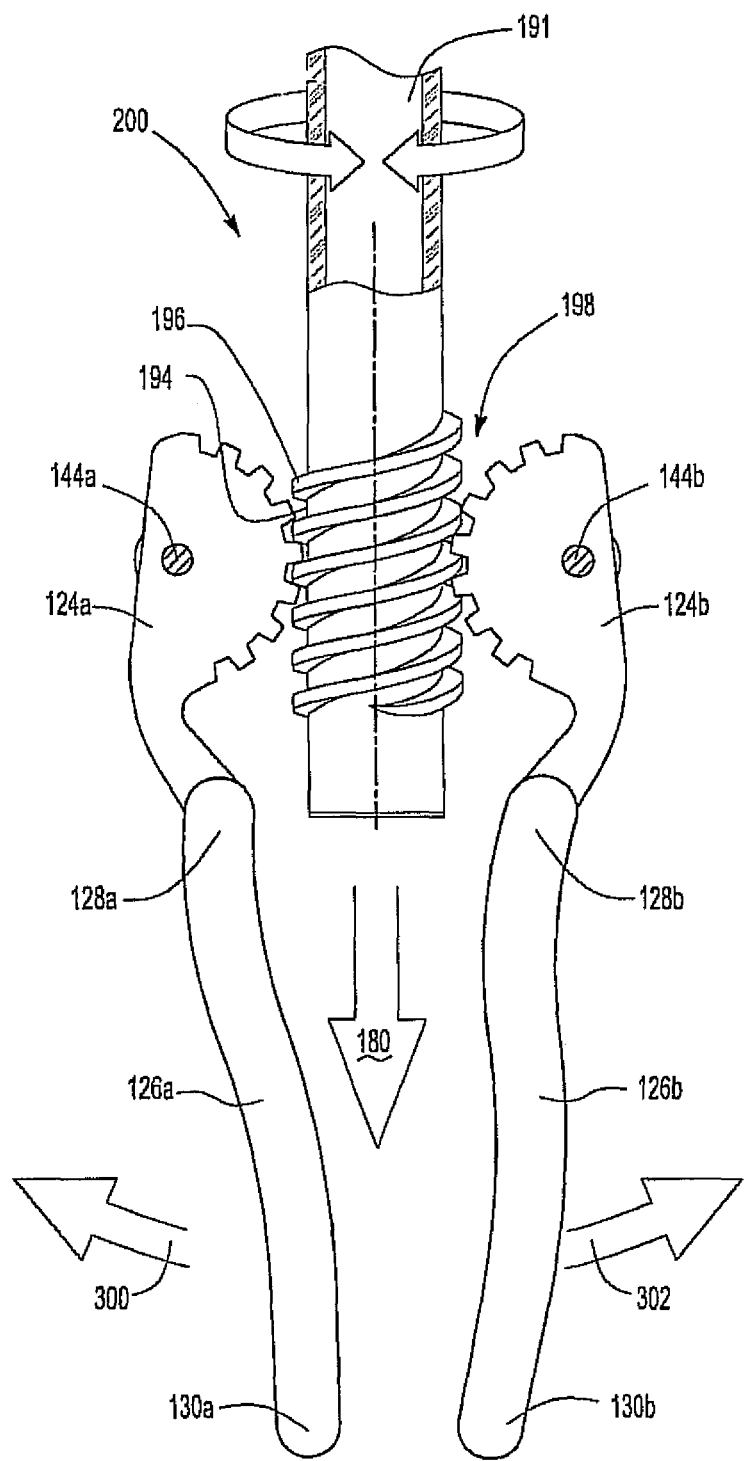
FIG. 5 illustrates a cross sectional side view of a second embodiment of the adjustable laryngeal mask utilizing a helical thread.

A preferred embodiment and numerous secondary and tertiary embodiments of the invention will now be described in reference to the figures.

An adjustable laryngeal airway (hereinafter referred to as ALA) is disclosed including a tube having a threaded portion, two arms having structure operable to connect to the threaded portion located on the tube, a connecting structure connecting the two arms to one another to secure the arms to the tube, and a mask fitted around the outer surface of the tube thereby permitting a seal over the human mouth. When the user of the apparatus twists or pushes the tube, the arms and structure on the arms are engaged with the threading on the outer surface of the tube thereby allowing the arms to rotate about a pivot point and allowing the arms to swing upwards and away from the tube to remove and displace any soft tissue located within the body which is preventing air flow into or out of the body.

FIGS. 1, 2 and 3 illustrate an adjustable laryngeal airway or ALA 10 of the present invention. The ALA 10 generally includes a tube 11 having a first end 12 and a second end 14. The tube 11 has a generally circular cross section and is comprised of a plastic, polymer, or polymer-like material operable to be sanitized or disposed after use. Threading 40 is provided near the second end 14 on the tube 11. The threading 40 includes a plurality of raised portions 18 and lowered sections 20 to provide a worm gear type thread and gear configuration disposed on the outer surface 92 of the tube 11. The raised portions 18 extend circumferentially around the outer circumference of the tube 11 generally at the second end 14 of the tube 11.

In the present embodiment, two arms 22a, 22b are utilized. The arms 22a, 22b each include first portions 24a, 24b and second portions 26a, 26b. The first portions 24a, 24h of the arms 22a, 22b include a rounded portion including a plurality of grooves 50 and raised portions 48. The grooves 50 and raised portions 48 on the rounded surface of the first portions 24a, 24b are operable to engage with the threaded portion 40 located on the outer surface 92 of the tube 11. By way of example, when the arms, primarily arm 22b, is in a fully rotated position wherein the arm 22b is generally perpendicular in relation to the tube 11, the raised portion 48 is located within the indentation 20 of the threading 18, 20 located on the tube 11.

Alternatively, the threading 40 is a plurality of parallel slots operable to engage the threading on the rounded portion 46.

The arms 22a, 22b further include the second or lower portions 26a, 26b. The second portions 26a, 26b further include a first portion 28a, 28b and a second portion 27a, 27b. The first portions 28a, 28b of the lower portions 26a, 26b of the arms 22a, 22b connect to the first portions 24a, 24b of the arms 22a, 22b. The second or lower portions 26a, 26b connect to the first portions 24a, 24b at an arm connector of the first portion 24a, 24b. The connecting portion of the upper portions 24a, 24b to the lower or second portions 26a, 26b connected to 28a, 28b may be connected by molding, adhesive, bolt, or other connection means. The connection at 28a, 28b must be secure and fixed so as to prevent movement between the first portions 24a, 24b and the second portions 26a, 26b.

The second portions 26a, 26b of the arms 22a, 22b include second portions 27a, 27b. When in use, the user inserts the second portions 27a, 27b of the arms 22a, 22b into the mouth and throat of the user. Each of the second portions 26a, 26b of the arms 22a, 22b includes curvature 32 so as to create a suction with the soft tissue located in either the mouth or the throat. The curvature 32 can also be disposed on opposite sides of the second portions 26a, 26b.

It is essential to the operation of the ALA 10 that a seal be created between the area external to the body and the area into the body. The mask 60 of the ALA 10 creates this required seal. The mask 60 includes an inflated portion 64. The inflated portion 64 includes a lower surface 64a. The lower surface 64a is the area making contact with the face of the patient when the ALA 10 is in use. The mask further includes a conical portion 62 wherein the inflated portion 64 is located at the largest portion of the conical portion 62. The mask further includes an open inner section 66 allowing the tube 11 to pass through. An upper portion 68 is provided on the mask 60. The upper portion 68 includes a strap connector 70 disposed below the first portion 68. The strap connector includes a plurality of prongs 70a, 70b, 70c. When in use, the mask 60 is secured to the patient's head by means of a strap 72. It is common to use a plurality of straps 72 to connect the mask 60 to the patient's head. A plurality of apertures 74 located on a strap member 73 of the main strap 72 is provided. The apertures connect 76 to the prongs 70a, 70b, 70c. The strap 72 then wraps around the patient's head to provide a secure connection of the mask 60 to the head of the patient.

The ring 42 connects the arms 26a, 26b securely to one another and around the tube 11. The ring 42 is operable to encompass the entirety of the tube 11 while simultaneously securing first portion 24a and second portion 24b of the arms 26a, 26b to one another and around the tube 11. The ring 42 includes a first portion 42a and a second portion 42b. The first portion 42a of the ring 42 includes a connection member 44a, such as a bolt, to secure the first portion 42a of the ring 42 to a first portion 24a of the arm 26a. Further, the ring 42 includes a second portion 42b operable to secure the ring 42 to the second portion 24b of the arm 26b by means of the connection member 44b.

FIG. 1A and FIG. 5 illustrates an alternative embodiment of an ALA. In this embodiment, the outer surface of the tube includes a helical thread 198. The helical thread 198 allows the user to rotate 190 the tube 192 to actuate the arms 126a, 126b. The ALA 200 as depicted in FIGS. 1A and 5 allows the user to rotate 190 the tube 192 thereby permitting the tube 192 to move 180 internal and external of the body. When the tube 192 is rotated 190, the tube 192 moves either upward or downward depending upon whether the tube 192 is rotated clockwise or counterclockwise. When the tube 192 is rotated 190 and the tube moves downwards 180, the arms 126a, 126b are rotated outwards 300, 302 away from the tube 192.

The tube 192 includes a helical thread 198 on the outer surface 193 of the tube 192. The helical thread 198 includes raised portions 196 with accompanying lower portions 194. The helical thread 198 extends over only a portion of the outer surface of the tube 192. The helical thread 198 may be adjusted in size and thickness so as to secure and tighten the arms 126a, 126b generally.

The ALA 200 further includes two arms 126a, 126b. The arms 126a, 126b include first portions 128a, 128b and second portions 130a, 130b. The arms 126a, 126b further include upper portions 124a, 124b. The upper portions 124a, 124b include a rounded portion 123 including a plurality of threads or grooves 146 similar to the threads or grooves 40 as illustrated in FIGS. 1 and 3. The threads 146 located on the rounded portions of the upper portions 124a, 124b of the arms 126a, 126b engage with the helical thread 198 located on the outer surface 193 of the tube 192.

A ring 142, 142a, 142b connects the first arm 126a to the second arm 126b at the first portion 124a and the second portion 124b. The ring 142 connects at pivot points 144a, 144b. The pivot points 144a, 144b may be a screw or other pivotable member. The ring 142 connects the arms 126a, 126b securely to the tube 192.

In yet another alternative embodiment as shown in FIG. 4, the ring 242 includes threading 202, 204. Threading 240 on the tube 293 engages with each other to either prevent movement or facilitate movement of the tube 293 as the user twists or pushes the tube 293. The threading 240 on the tube 293 includes raised portions 218 and indented portions 220 operable to fit within the threading or tongue-and-groove configuration located on the ring 242. The threading located on the ring 242 includes raised portions 204 and indented portions 202 operable to engage with the raised portions 218 and indented portion 220 located on the outer surface 293 of the tube 292. The tube 292 includes an inner surface 290 and an outer surface 293. The ring 242 further connects to the arms by means of the connector 244.

In an additional embodiment, the ALA 10 as detailed above further includes a balloon 91a located on the outer surface of the arm 26a or 26b or two balloons 91a, 91b, one on each arms 26a and 26b. The balloon 91a, 91b is inflated by means of previously known auxiliary pumps and inflation syringes. As shown in FIG. 4, the balloon 91a on arm 26a serves to create a seal around the esophageal proximal opening, thus preventing the entry of air into the stomach (the esophagus is a soft tube like structure, located anterior to the larynx and trachea and connects the mouth to the stomach). The balloon 91b on the arm 26b would adhere against the hard and soft palates in the ceiling of the mouth and thus prevent any trauma that may result from the continuous pressure exerted by the arm 26b.

In yet another additional embodiment, an aperture 80 is located on the tube 11. The aperture 80 is large enough in diameter to permit a catheter to pass through the aperture 80. The catheter passes though the center of the tube 11, though the inner surface (90, 191, 290) and further passes though the aperture 80. The catheter is used to suction saliva out of a patient's mouth. The aperture 80 further includes a seal 82 operable to prevent air or liquid from entering the tube 11. The seal 82 is a flexible or elastic annular ring having an outer diameter and an inner diameter. The inner diameter of the seal 82 tightly connects to the catheter when the catheter is in place. The outer diameter of the seal 82 is connected to the tube 11.

Figure 6:
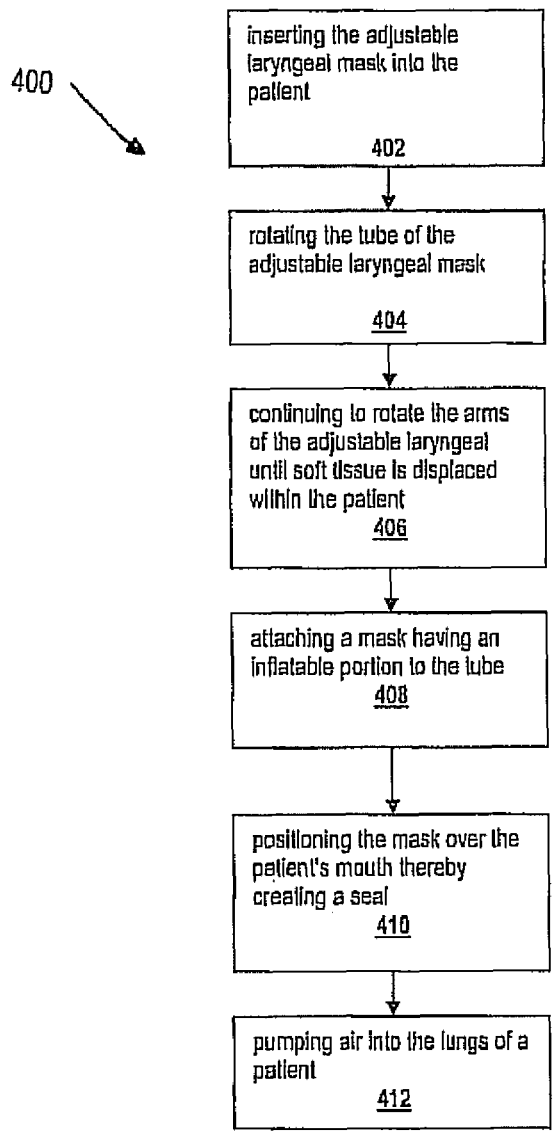
FIG. 6 is a flow chart illustrating the method of the appended claims.

A method 400 of resuscitating a patient using an adjustable laryngeal mask airway is illustrated in FIG. 6. The method includes the first step of inserting 402 the adjustable laryngeal mask into the patient so that the mask is positioned adjacent the patent's laryngeal inlet. Next, the method 400 requires rotating the tube 404 of the adjustable laryngeal mask to as to engage rotation of the arms and continuing to rotate 406 the arms of the adjustable laryngeal until soft tissue is displaced within the patient, attaching 408 a mask having an inflatable portion to the tube.

The method next requires the step of positioning 410 the mask over the patient's mouth thereby creating a seal. The method further includes the step of pumping 412 air into the lungs of a patient by means of an air bag or equivalent air providing means. The pumping 412 requires the use of an air bag attached to the first end 12 of the tube 11. The method may further include the step of attaching the mask 60 to the patient by means of the straps 72.

The ALA 10 in its operational position can be used to have a regular EIT over a fiberoptic scope inserted through the tube toward the trachea. This will allow securing of the airway with a regular EIT, with direct vision through the fiberoptic scope, in a non-emergency situation, while intermittently ventilating with an ALA.

The invention is not restricted to the illustrative examples and embodiments described above. The embodiments are not intended as limitations on the scope of the invention. Methods, apparatus, compositions, and the like described herein are exemplary and not intended as limitations on the scope of the invention. Changes therein and other uses will occur to those skilled in the art. The scope of the invention is defined by the scope of the claims.

The invention claimed is:

1. An airflow control apparatus to control air flow into the body, specifically into the lungs, the airflow control apparatus comprising:
    a tube having an inner surface and an outer surface, the inner surface of the tube permitting air flow, the outer surface having a thread;
    at least one arm having a first portion and a second portion, the first portion spaced laterally apart from the second portion, the at least one arm having structure operable to connect with the thread on the outer surface of the tube;
    a ring connecting the at least one arm, the ring connected at the first portion of the at least one arm; and
    a facemask fitted around the outer surface of the tube;
    wherein the user of the airflow control apparatus is able to twist the tube thereby engaging the thread on the outer surface of the tube to allow the at least one arm to pivot about the first portion thereby operable to displace soft tissue blocking the airway of a patient.

2. The airflow control apparatus of claim 1 wherein the thread on the outer surface of the tube is a helical thread operable to tighten and lock.

3. The airflow control apparatus of claim 1 wherein the thread on the outer surface of the tube is a worm gear.

4. The airflow control apparatus of claim 1 wherein the ring includes threads operable to engage with the threads disposed on the outer surface of the tube.

5. The airflow control apparatus of claim 1 wherein the second portion of the at least one arm is curved to facilitate suction to improve displacement of soft tissue.

6. The airflow control apparatus of claim 1 wherein the airflow control apparatus is composed of a disposable material.

7. The airflow control apparatus of claim 1 wherein the airflow control apparatus is composed of a plastic.

8. The airflow control apparatus of claim 1 wherein the airflow control apparatus is composed of a polymer.

9. The airflow control apparatus of claim 1 wherein the first portion of the at least one arm is rounded.

10. The airflow control apparatus of claim 9 wherein the rounded portion of the first portion of the at least one arm includes a plurality of grooves to facilitate connection and rotation of the at least one arm on the outer surface of the tube.

11. The airflow control apparatus of claim 9 wherein the rounded portion of the first portion of the at least one arm is threaded to facilitate connection and rotation of the at least one arm on the outer surface of the tube.

12. The airflow control apparatus of claim 9 wherein the rounded portion of the first portion of the at least one arm includes a plurality of slots to facilitate connection and rotation of the at least one arm on the outer surface of the tube.

13. The airflow control apparatus of claim 1 wherein the at least one arm includes at least one inflatable balloon to create a seal around the esophageal opening thus preventing air entry into the stomach.

14. The airflow control apparatus of claim 1 wherein the outer surface of the tube includes an aperture.

15. The airflow control apparatus of claim 14 wherein the aperture includes a seal operable to securely seal a catheter passes through the aperture.

16. The airflow control apparatus of claim 1 wherein the at least one arm is curved to create a seal around the esophageal opening thus preventing air entry into the stomach.

17. A method of resuscitating a patient comprising the steps of:
providing an airflow control apparatus according to claim 1, wherein the airflow control apparatus further comprises an adjustable laryngeal mask;
inserting the adjustable laryngeal mask into the patient so that the adjustable laryngeal mask is positioned adjacent the patient's laryngeal inlet;
rotating the tube of the airflow control apparatus so as to engage rotation of the at least one arm;
continuing to rotate the at least one arm of the airflow control apparatus until soft tissue is displaced within the patient;
attaching the facemask having an inflatable portion to the tube;
positioning the facemask over the patient's mouth thereby creating a seal; and
pumping air into the lungs of the patient.

* * * * *